(12) United States Patent
Potyrailo et al.

(10) Patent No.: US 6,538,725 B2
(45) Date of Patent: Mar. 25, 2003

(54) METHOD FOR DETERMINATION OF STRUCTURAL DEFECTS OF COATINGS

(75) Inventors: Radislav Alexandrovich Potyrailo, Niskayuna, NY (US); Daniel Robert Olson, Voorheesville, NY (US); Michael Jarlath Brennan, Burnt Hills, NY (US); James Norman Cawse, Pittsfield, MA (US); Bret Ja Chisholm, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 242 days.

(21) Appl. No.: 09/765,757

(22) Filed: Jan. 22, 2001

(65) Prior Publication Data

US 2002/0135758 A1 Sep. 26, 2002

(51) Int. Cl.[7] .......................... G01B 11/16; G01N 21/00
(52) U.S. Cl. ....................... 356/32; 356/237.2
(58) Field of Search .................. 356/32, 237.1, 356/237.2, 237.5; 250/302; 73/762, 800

(56) References Cited

U.S. PATENT DOCUMENTS

| | | | | |
|---|---|---|---|---|
| 3,995,157 A | * | 11/1976 | Holub et al. | 250/302 |
| 4,004,456 A | | 1/1977 | Vahaviolos | 73/71.4 |
| 4,168,249 A | | 9/1979 | Meyer | 260/16 |
| 4,255,308 A | | 3/1981 | Brasen | 260/29.6 RW |
| 4,541,287 A | | 9/1985 | Roper | 73/827 |
| 4,612,805 A | | 9/1986 | Bruce et al. | 73/150 A |
| 4,996,076 A | | 2/1991 | Nakaya et al. | 427/38 |
| 5,027,650 A | | 7/1991 | Oblas et al. | 73/150 A |
| 5,098,750 A | | 3/1992 | Ueno et al. | 428/304.4 |
| 5,454,260 A | | 10/1995 | Wang | 73/150 A |
| 5,513,537 A | | 5/1996 | Brooks et al. | 73/865.8 |
| 5,573,909 A | | 11/1996 | Singer et al. | 435/6 |
| 5,725,960 A | | 3/1998 | Konishi et al. | 428/451 |

(List continued on next page.)

OTHER PUBLICATIONS

Standard Test Methods for Measuring Adhesion by Tape Test; ASTM Designation: D3359–97; pp. 367–374.
Standard Practice for Testing Water Resistance of Coatings Using Water Immersion; ASTM Designation D870–97; pp. 84–86.
Characterizaton of polymers; Chou, N.J. et al, Butterworth–Heinemann., Boston, MA 1994, p. 222.
*Thermoplastic Polymer Additives. Theory and Practice;* Lutz, J.T., Jr., Ed.; Marcel Dekker: New York, NY Chapter 3, 1989.
Paint and Coating Testing Manual; Koleske, J.V., Ed.; American Society for Testing and Materials: Philadelphia, PA, Chapters 44 and 45, 1995.
Wicks, .W., Jr. et al., *Organic Coatings: Science and Technology;* Wiley: New York, NY, Chapter 28, 1999.

*Primary Examiner*—Michael P. Stafira
(74) *Attorney, Agent, or Firm*—Noreen C. Johnson; Christian G. Cabou

(57) ABSTRACT

The present invention provides a method for quantifying structural defects of a coating composition on a given substrate, where certain structural defect-inducing tests are performed. In this method, a coating formulation is doped with a colorimetric or luminescent material. Concentration of the material depends on the quantum efficiency, excitation and emission wavelengths, and employed detection techniques, and can range from about 1 fM to about 1 mM. Before, during and/or after such tests, the coating is illuminated with a wavelength of radiation at which the reflected or transmitted color or emitted luminescence of the material in the coating is detectable with an optical detector or by visual inspection. In this fashion, the percentage of failure of the coating can be quantified as well as the level of interdiffusion of coating into substrate or substrate into coating. The method of the invention is thus particularly well-suited for the combinatorial analysis of an array of coating samples. Additionally, when the structural defect-inducing material test is being performed, the removed coating material can be analyzed in like fashion.

50 Claims, 6 Drawing Sheets

U.S. PATENT DOCUMENTS

| | | |
|---|---|---|
| 5,817,732 A | 10/1998 | Asahina et al. .............. 528/45 |
| 5,829,804 A | 11/1998 | Sacki et al. ................ 293/120 |
| 6,072,568 A * | 6/2000 | Paton et al. .................. 356/32 |
| 6,327,030 B1 * | 12/2001 | Ifju et al. .................... 356/32 |

* cited by examiner

METHOD FOR DETERMINATION OF STRUCTURAL DEFECTS OF COATINGS

Portions of this work were funded by the National Institutes of Standards and Technology (NIST) under U.S. Government Contract No. 70NANB9H3038.

BACKGROUND OF THE INVENTION

This invention discloses a method for quantification of structural defects of transparent thin coating libraries. Such structural defects are induced before, during and/or after certain performed tests.

The amount of energy required to separate a coating from its substrate, i. e. adhesion, is important in the selection of compatible materials for a variety of applications. These applications include finishing the exteriors of automobile and truck bodies, appliances, electronic parts, and other high-quality products. Adhesion of a coating is affected by several factors, which include interdiffusion of materials across the interface between the substrate and the coating, compound formation at the interface, coating and substrate morphologies, defect structures, and residual stresses. Absolute determination of these factors, their interdependence, and the resulting influence on the mechanical properties of the interfacial region is the subject of ongoing research. Thus, coating adhesion to a substrate is typically determined empirically. The standard test methods include tape test, scrape test, peel test, pull-off test, scratch test, indentation test, lap shear test, bend test, blister test, and water immersion test, as well as many others. (See, for example, ASTM D 3359 and ASTM D 870).

Other important parameters of the coating properties include abrasion resistance, elongation, and tensile strength, all of which are empirical indicators of the inherent qualities of a given coating composition to remain adhered to the substrate and, as well, to maintain its own structural integrity as a polymeric matrix. Conventional methods for elongation measurements are typically based on mandrel bend tests, where a coating is deposited onto the surface of a substrate, manually inserted into a test apparatus, and bent at different radii. The evaluation of a coating is performed visually by observing the cracks. Similarly, tensile properties of coatings are evaluated as a function of crack formation.

Reliable evaluation of these parameters of transparent thin coatings presents an analytical measurement challenge. Thus, the need exists to provide methodology for the rapid determination of such parameters.

SUMMARY OF THE INVENTION

To quantify structural defects of transparent thin coating libraries, induced before, during and/or after the performed tests, a liquid coating formulation or powder coating formulation is doped with a colorimetric or luminescent dye. Concentration of the dye depends on the quantum efficiency of the dye, excitation and emission wavelengths, and employed detection techniques, and can range from about 1 fM to about 1 mM. Before, during and/or after the tests, the coating is illuminated with a wavelength of radiation at which the reflected color or luminescence of the dye in the coating is detectable with an optical detector or by visual inspection. In a preferred embodiment, the structural defect which is analyzed is the coating's inherent structural adhesion or interdiffusion. As used herein, "inherent structural defect or adhesion" refers to the inherent capability of a coating composition to remain intact on a given substrate or to remain adhered to a given substrate, respectively, when subjected to the "structural defect inducing tests" as set forth herein. "Interdiffusion" is the diffusion of both coating and substrate materials across the coating-substrate interface (Chou, N. J.; Kowalczyk, S. P.; Saraf, R.; Tong, H.-M., Characterization of polymers. Butterworth-Heinemann, Boston, Mass., 1994. p. 222). Interdiffusion results in an interphase which consists of polymer chain segments from both contiguous phases. (*Paint and Coating Testing Manual;* Koleske, J. V., Ed.; Americal Society for Testing and Materials: Philadelphia, Pa., 1995, chapter 44).

A suitable automatic measurement system includes a light source, photodetector and a computer to analyze the recorded signal and to relate it to the amount of coating or coating integrity after testing.

Multiple tests can be combined in a single operation. For example, adhesion and abrasion tests can be done in a single step where a coating library is exposed to a stream of abrasive particles in a fluid.

B indicates irradiation of one wavelength, $hv_1$, and the passage of that particular wavelength through the coating and substrate, along with the luminescence of a different wavelength ($hv_2$) passing through the substrate.

Similarly, C depicts the irradiation of a sample and the passage of light of a given wavelength ($hv_1$) through the coating and sample and the emission of luminescence of a different wavelength ($hv_2$).

D depicts the excitation of the coating with irradiation of one wavelength ($hv_1$) and the luminescence with light of a different wavelength ($hv_2$).

E depicts the irradiation of a sample with light of one wavelength ($hv_1$) and the collection of light of the same wavelength ($hv_1$) at a 360° angle to the emitted light.

Similarly, F depicts the irradiation of a sample with light of a given wavelength ($hv_1$) and the collection of luminescence light of a different wavelength ($hv_2$) at a 360° angle to the emitted light.

G and I depict the irradiation of a sample with light of a given wavelength ($hv_1$) and the collection of light at a different collection angle (G) and at multiple collection angles (I).

Similarly, H and J, depict the irradiation of a sample with light of a given wavelength ($hv_1$) and the collection of luminescence of a different wavelength ($hv_2$) at a different collection angle (H) and at multiple collection angles (J).

Figure 5:
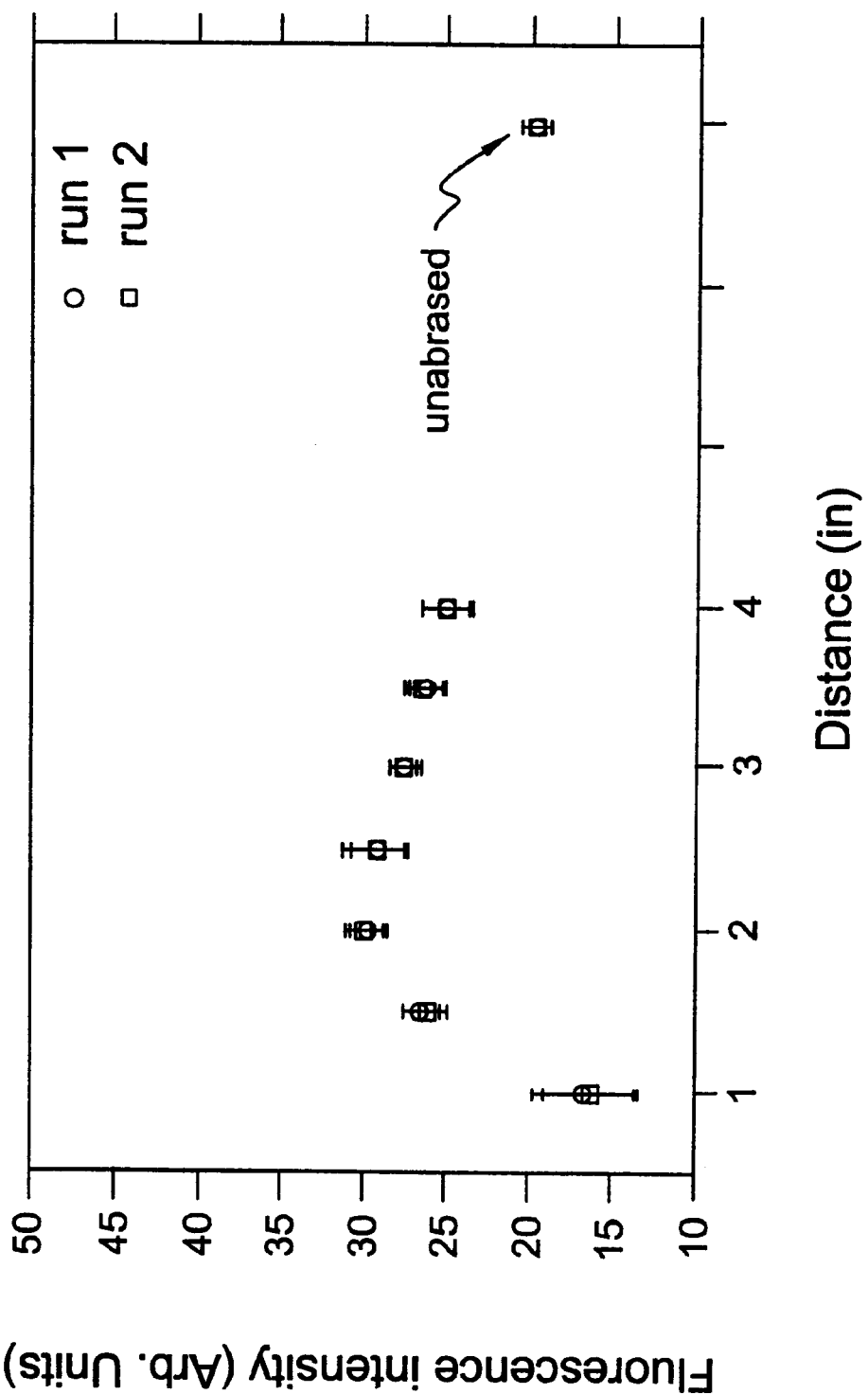

FIG. 5 demonstrates the variation of intensity of luminescence from the coating as a function of coating/sand blaster distance. The error bars are one standard deviation from the mean of measurements of 11 array elements abraded with the same conditions. (a whole row of coatings)

Figure 6:
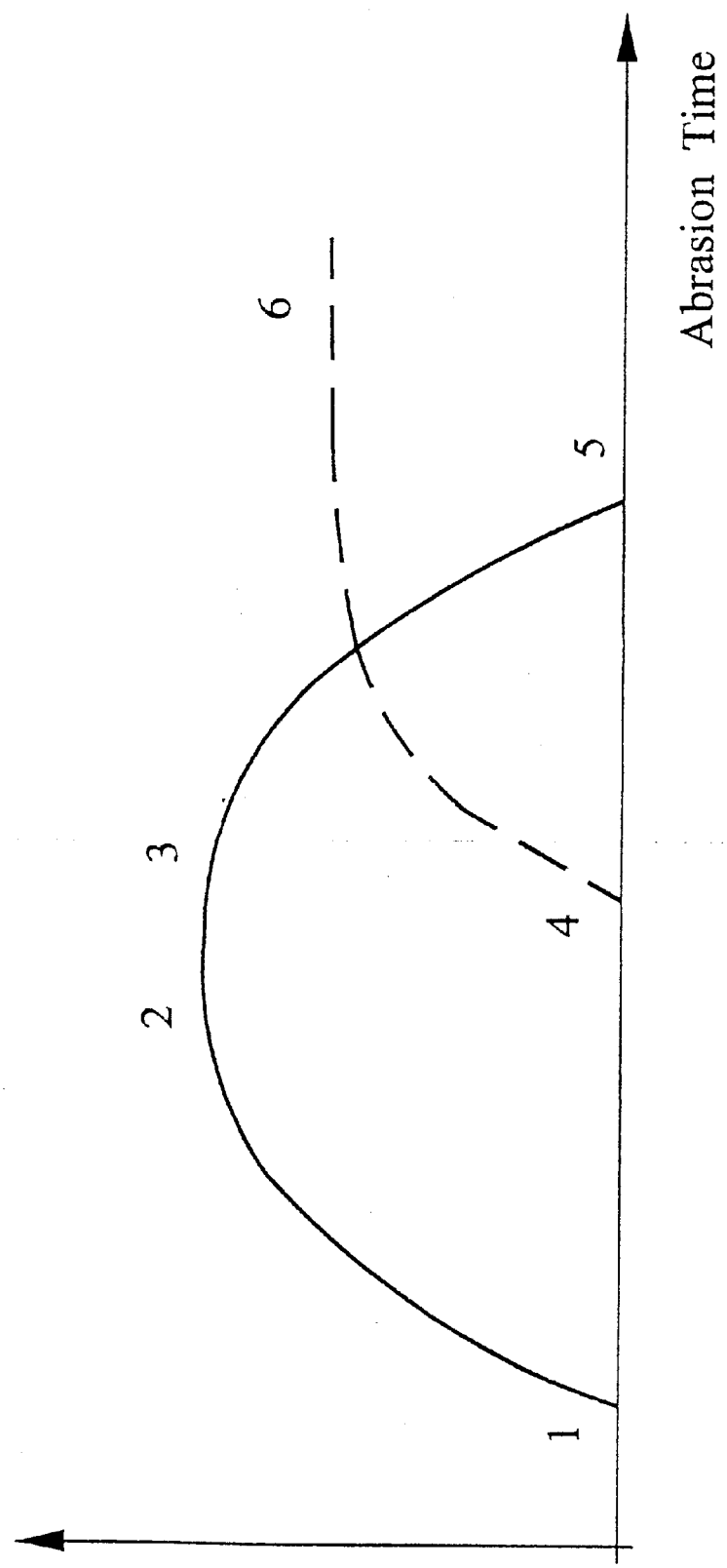

FIG. 6 depicts a typical time-dependent evolution of spectroscopic signals during the abrasion test from the coating (solid line) and from the substrate (dotted line). From the beginning of the abraded region (point 1), the signal from the coating increases until it reaches a steady state level (point 2). Time delay between the time point when signal reached the steady signal (point 2) and time point when it starts to decrease (point 3) depends on coating thickness and abrasion conditions. After time point 3, the signal associated with the substrate starts to increase, because part of an abraded material now contains the substrate (point 4). The signal from the substrate increases until it reaches an equilibrium (point 6). In this point, all the coating has been abraded (point 5).

DETAILED DESCRIPTION OF THE INVENTION

The present invention provides a method for quantifying inherent structural defects of a coating composition on a given substrate, which comprises:

(a) providing at least one coating sample having incorporated therein at least one colorimetric or luminescent material;

(b) irradiating said coating sample with light of a pre-selected wavelength, before, during and/or after subjecting said sample to at least one structural defect-inducing test;

(c) collecting spectral data emitted from said sample; and (d) applying a pre-determined test to said spectral data to determine whether said sample meets pre-selected criteria.

In the method of the present invention, the spectral data obtained from these tests is an indication of the inherent structural qualities of the coating composition itself on a given substrate. Thus, when such a coating composition is formulated into a transparent composition, doped with the colorimetric or luminescent material and coated on a substrate, the measurements as set forth herein provide data which indicate the composition's ability to maintain adhesion to the surface as well as its ability to remain as an intact polymeric matrix. Thus, in a preferred embodiment, there is provided the methods of the present invention as a method for determining the inherent structural adhesion and inter-diffusion of a given polymeric coating matrix on a given substrate. In this regard, referring above to the description of interdiffusion above, when the coating has been removed and the spectral data has reached a new baseline, i.e., has reached a constant level, the difference (Δ) between this baseline and the spectral data obtained from analysis of uncoated substrate will thus represent the quantification or amount of interdiffusion of coating into the substrate. As noted below, one can alternatively analyze the removed coating material, during, for example, abrasion, and in like fashion analyze the amount of substrate so removed, which represents the amount of interdiffusion of substrate into the coating. Thus in a further embodiment, there is provided a method for determining the extent of interdiffusion of the coating into the substrate, which comprises applying steps (a) through (c) above, followed by (d) comparing a steady state baseline achieved after removal of coating to a spectral data acquired by irradiation of an uncoated substrate.

Examples of suitable colorimetric or luminescent materials include known dyes such as polyazaindacenes or coumarins, including those set forth in U.S. Pat. No. 5,573,909, incorporated herein by reference. Other suitable families of dyes include hydrocarbon and substituted hydrocarbon dyes; polycyclic aromatic hyrdocarbons; scintillation dyes (preferably oxazoles and oxadiazoles); aryl- and heteroaryl-substituted polyolefins ($C_2$–$C_8$ olefin portion); carbocyanine dyes; phthalocyanine dyes and pigments; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; and xanthene dyes.

The following is a partial list of commercially available, suitable luminescent dyes.

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4-Bis-(2-butyloctyloxy)-p-quaterphenyl p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'-Dimethyl-p-quaterphenyl
2,2-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzo-thiazolium Perchlorate
2-(6-(p-Dimethylaminophenyl)-2,4-neopentylene- 1,3,5-hexatrienyl)-3-methylbenzothiazolium Perchlorate
2-(4-(p-Dimethylaminophenyl)-1,3-butadienyl)- 1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
N-Methyl-4-trifluoromethylpiperidino-<3,2-g>coumarin
3-(2'-N-Methylbenzimidazolyl)-7-N,N-diethyaminocoumarin
2-(1-Naphthyl)-5-phenyloxazole
2,2'-p-Phenylen-bis(5-phenyloxazole)
3,5,3'''',5''''-Tetra-t-butyl-p-sexiphenyl
3,5,3'''',5''''-Tetra-t-butyl-p-quinquephenyl
2,3,5,6-1H,4H-Tetrahydro-9-acetylquinolizino-<9,9a,1-gh>coumarin
2,3,5,6-1H,4H-Tetrahydro-9-carboethoxyquinolizino-<9,9a,1-gh>coumarin
2,3,5,6-1H,4H-Tetrahydro-8-methylquinolizino-<9,9a,1-gh>coumarin
2,3,5,6-1H,4H-Tetrahydro-9-(3-pyridyl)-quinolizino-<9,9a,1-gh>coumarin
2,3,5,6-1H,4H-Tetrahydro-8-trifluoromethylquinolizino-<9,9a,1-gh>coumarin
2,3,5,6-1H,4H-Tetrahydroquinolizino-<9,9a,1-gh>coumarin
3,3',2'',3'''-Tetramethyl-p-quaterphenyl
2,5,2'''',5''''-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene
9,10-diphenylanthracene
Pyrene
Chrysene
Rubrene
Coronene
Phenanthrene
Fluorene
Aluminum phthalocyanine and
Platinum octaethylporphyrin.

In the practice of the invention, organic and inorganic colorimetric and luminescent particles which are insoluble can be doped into the coating and/or substrate. These particles can be pigments, metal and semiconductor nanoparticles, nanotubes, nanowires, etc. These materials provide color and/or luminescence which can have higher long-term stability and are less responsive to photobleaching. See also, *Thermoplastic Polymer Additives. Theory and Practice;* Lutz, J. T., Jr., Ed.; Marcel Dekker: New York, N.Y., 1989, which provides a typical list of some inorganic and organic pigments.

Examples of inorganic pigments include but are not limited to the following:
carbon black
bone black
manganese violet
ultramarine blue cobalt aluminate
chromium oxide
chrome yellow
cadmium yellow
molybdate orange
red iron oxide
cadmium red Examples of organic pigments include but are not limited to the following:
carbazole dioxazine violet
quinacridone violet
diarylide yellows
disazo yellows
isoindolinone yellows
disazo reds
perylene red Examples of nanoparticles include but are not limited to the following materials: CdS, ZnS, $Cd_3P_2$, PbS, and combinations thereof.

In a preferred embodiment, dyes and luminophores such as LUMOGEN F, available from BASF, Yellow dye 083, Orange dye 240, Red dye 300, and Violet dye 570 are utilized.

Further, it is preferred that in order to provide data which is most useful, the coating or film which is formed on the substrate is of a consistent thickness for each grouping or array of coating samples. Alternatively, the thickness of the sample can be varied, as in an array, so long as the thickness is taken into account when the spectral data so obtained is appropriately analyzed.

As noted above, the coating sample is irradiated with light of a pre-selected wavelength. The choice of wavelength will of course be determined by the choice of colorimetric material or luminescent material so utilized. In the case of colorimetric materials, the photodetector will be adapted to collect reflected and/or transmitted visible light and in association with a microcomputer and appropriate software, will analyze and quantify the visible spectral data so obtained.

Visible spectral data collected in the presence of a colorimetric material in the coating will contain a spectral signature of the material. The spectral signature (absorbance, transmission, etc.) is obtained for example by collecting a spectrum from a region of interest and referencing this spectrum to a spectrum of a region of coating on a substrate free from the colorimetric material (background spectrum). The region of interest can be a region with a coating or a region with a known interdiffusion level after coating removal. The spectra from the region of interest and the region free from the colorimetric material (background spectrum) are further related to extract the information about the presence of the colorimetric material in the region of interest. This relation can be obtained by subtracting two relevant spectra or by other known methodologies.

When a luminescent material is utilized, the wavelength chosen will be that which will provide detectable luminescence. The emitted luminescent light will be analyzed in like fashion.

The term "structural defect-inducing tests" as used herein refers to any of the known methodologies used to empirically analyze abrasion and adhesion of a coating to a substrate. As general categories of such tests, we mean a test which utilizes at least one defect-inducing method selected from sonication, water immersion, falling abrasive test, abrasive blast test, rotating discs test, and rectilinear motion test, tape test, scrape test, peel test, pull-off test, scratch test, indentation test, lap shear test, bend test, blister test, as well as many others. Details of such tests can be found in *Paint and Coating Testing Manual;* Koleske, J. V., Ed.; Americal Society for Testing and Materials: Philadelphia, Pa., 1995, chapters 44 and 45. As noted above, such methodologies include the pull test, peel test, micro-scratch test, linear-rub test, torsion-rub test, and many others. The standard test methods include the tape test, scrape test, peel test, pull-off test, and water immersion test (See ASTM D 3359 and ASTM D 870).

The "pull test" is illustrated in U.S. Pat. No. 4,541,287, incorporated herein by reference.

The "peel test" is illustrated in U.S. Pat. No. 4,612,805, incorporated herein by reference.

The "micro scratch test" is illustrated in U.S. Pat. No. 5,027,650, incorporated herein by reference.

The "supersonic water jet test" is illustrated in U.S. Pat. No. 5,454,260, incorporated herein by reference.

The "crosscut test" is illustrated in U.S. Pat. No. 5,725,960, incorporated herein by reference. In general, the coated substrate is cut with a cutter making eleven cuts at intervals of 1 mm in one direction and then these cuts were crosscut with eleven cuts at intervals of 1 mm which are perpendicular to the original cuts, thereby making 100 squares of 1×1 mm. Subsequently, a cellophane pressure sensitive tape such as that sold by Sekisui Chemical Company, Ltd., (or other commercially-available pressure sensitive tape) is applied to the coated substrate and the tape is then peeled by a force applied in perpendicular fashion to the surface of the coated substrate. The result is shown by the number of squares remaining on the surface of the coated substrate, per 100 squares.

The "contrast analysis test" is illustrated in U.S. Pat. No. 5,513,537, incorporated herein by reference.

The methodology of the present invention is thus useful for analyzing in rapid fashion large arrays or combinatorial libraries of coatings samples which are desired to be evaluated for their adhesion properties. Moreover, such arrays could also provide variation on the substrate itself, the presence or lack of adhesion-promoting substances, etc.

Furthermore, the variation of coating-deposition and curing conditions can be also induced on a single substrate with a plurality of coatings. Yet furthermore, the variation of test conditions can be induced on a single substrate with a plurality of coatings.

Thus, in a preferred embodiment, there is provide a method for quantifying inherent structural defect of coatings in an array of samples coated with coating compositions on at least one given substrate, which comprises:

(a) providing an array of coating samples having incorporated therein at least one colorimetric or luminescent material;

(b) irradiating said array of coating samples with light of a pre-selected wavelength, before, during and/or after subjecting said array of samples to at least one structural defect-inducing test;

(c) collecting spectral data emitted from said array of coating samples; and (d) applying a pre-determined test to said spectral data to determine which of said samples meet pre-selected criteria.

In this embodiment, it is possible to vary the individual members of the array by coating substrate and/or structural defect-inducing test, thereby enabling the collection of a variety of data about a given coating composition's inherent adhesion characteristics to different substrates under a variety of adverse test conditions.

In the practice of the present invention, it is possible to quantify structural defects of a surface coating even before gross, visibly noticeable defects have occurred. Structural defects which are undetectable using visual inspection may be identified using the method of the present invention, by virtue of subtle changes in the incident reflected, transmitted or luminescence light (i.e., the spectra data) emanating from the sample or passing through the sample.

In the practice of the present invention, it is possible to quantify structural defects of a surface coating by virtue of subtle changes in the incident reflected, transmitted or luminescence light (i.e., the spectra data) emanating from the material that was used for coating testing. In this manner, any number of pre-selected criteria may be utilized to analyze an individual coating or array of coating samples, ranging from slight changes in spectral data to the total failure of a coating, in which case, no colorimetric or luminescent dye would be present to emit spectral data. Such materials can be, for example:

(a) tape used for tape-pull and other types of adhesion or other types of measurements, or (b) particles and/or fluids used for adhesion measurements by water jets, sandblaster, Taber, oscillating sand, and other tests.

Analysis of removed coating material generated during the test step provides a measurement capability when a small luminescence signal associated with a luminescent fraction of the removed material (coating or substrate) is observed in presence of a small background of material used for testing that does not generate luminescence.

In a further embodiment, the sample to be analyzed may be subjected to at least one structural defect-inducing test, and the coating material which is removed by such test(s) may be analyzed and spectral data collected.

Thus, in this further embodiment, there is provided a method for quantifying inherent structural defects of a coating composition comprised of a given material on a given substrate, which comprises:

(a) providing at least one coating sample comprising a substrate having coated thereon at least one coating material, said coating material having incorporated therein at least one colorimetric or luminescent material;

(b) subjecting said sample to at least one structural defect-inducing test, while collecting coating material which is removed from said sample by said test;

(c) irradiating said removed coating material with light of a pre-selected wavelength;

(d) collecting spectral data emitted from said removed coating material; and (e) applying a pre-determined test to said spectral data to determine whether said sample meets pre-selected criteria.

In analogous fashion to the analysis of the coating samples, the material removed from the coating may be analyzed and spectral data obtained so as to quantify the amount of coating so removed. As with the first embodiment described above, interdiffusion of the substrate into the coating can also be quantified. Thus, in a further embodiment, there is provided a method for quantifying interdiffusion of substrate into a coating material, which comprises applying steps (a) through (d) above, followed by (e) comparing a steady state spectral data baseline achieved after removal of coating to spectral data acquired by irradiation of a coating which has not been subjected to said at least one structural defect-inducing test.

Further, the amounts of coating and substrate removed during the abrasion test can be determined individually if the coating and substrate are doped with luminophore materials with different specific signatures. These signatures can have different spectral emission profiles, luminescence lifetimes, and luminescence polarization properties. These different luminescence signatures provide the capability for individual determination of the amounts of removed coating and substrate. Also, monitoring the luminescence as a function of time of the abrasion process, it is possible to assess the abrasion resistance of coatings by relating the time needed to reach the substrate through the total removal of the coating.

FIG. 6 depicts a typical time-dependent evolution of spectroscopic signals during the abrasion test from the coating (solid line) and from the substrate (dotted line). From the beginnings of the abraded region (point 1), the signal from the coating increases until it reaches a steady state level (point 2). Time delay between the time point when signal reached the steady signal (point 2) and time point when it starts to decrease (point 3) depends on coating thickness and abrasion conditions. After time point 3, the signal associated with the substrate starts to increase, because part of an abrasion material now reaches the substrate (point 4). The signal from the substrate increases until it reaches an equilibrium (point 6). At this point, all the coating has been removed by the abrasion (point 5).

In a preferred embodiment, such coatings can be irradiated with visible or UV or near infrared light and the emitted or transmitted radiation collected by a suitable photodetector associated with a computer which, when equipped with appropriate software, is capable of analyzing such data.

As a suitable light source, a 450-W Xe arc lamp from SLM Instruments, Inc., Urbana, Ill., Model FP-024) can be used coupled to a monochromator for selection of the excitation wavelength (SLM Instruments, Inc., Model FP-092). Spectral data can be collected for example using a spectrofluorometer (Ocean Optics, Inc., Dunedin, Fla., Model ST2000) and/or a CCD camera from Roper Scientific (Trenton, N.J., Model TE/CCD 1100 PF/UV).

For analysis of spectral features, software( available from Ocean Optics, Inc. (Dunedin, Fla.) can be used. For analysis of images, software from Roper Scientific (Trenton, N.J.), IMAQ Vision Builder from National Instruments (Austin, Tex.), Matlab (The Mathworks Inc., Natick, Mass.) can be used. Other software packages are available also from a variety of sources.

For a given sample, the initial irradiation will provide emission data, in either the visible, UV, or near infrared regions, which will establish a baseline. As the structural defect-inducing tests are conducted, additional data is collected until such time as a pre-selected level of the failure of the coating has been achieved.

By way of example, a transparent coating doped with LUMOGEN F, can be irradiated with UV, visible, and near infrared light and luminescence emission spectral data collected over time. The coating sample can then be subjected to elongation testing utilizing the known mandrel bend testing method. Such spectral data is continuously or periodically collected until such time as a new baseline is achieved, thereby signifying failure of the coating.

Similarly, in other tests, such as water immersion, water jet, tape, and crosscut tests, such tests can be performed on a given sample and such sample evaluated before, during and/or after such test has been completed and spectral data analyzed to quantify the percentage of the transparent coating which remains adhered to the substrate.

The method of the present invention may be utilized to quantify the adhesion properties of relatively hard coatings as well as relatively soft coatings. In this regard, the relative hardness/softness of a coating may be measured using the Pencil hardness test, which is determined using ASTM D 3363. The hardness is reported as the hardest pencil which will not cut into the coating. The results are expressed according to the following scale: (softest) 6B, 5B, 4B, 3B, 2B, B, HB, F, H, 2H, 3H, 4H, 5H, 6H (hardest).

Figure 1:
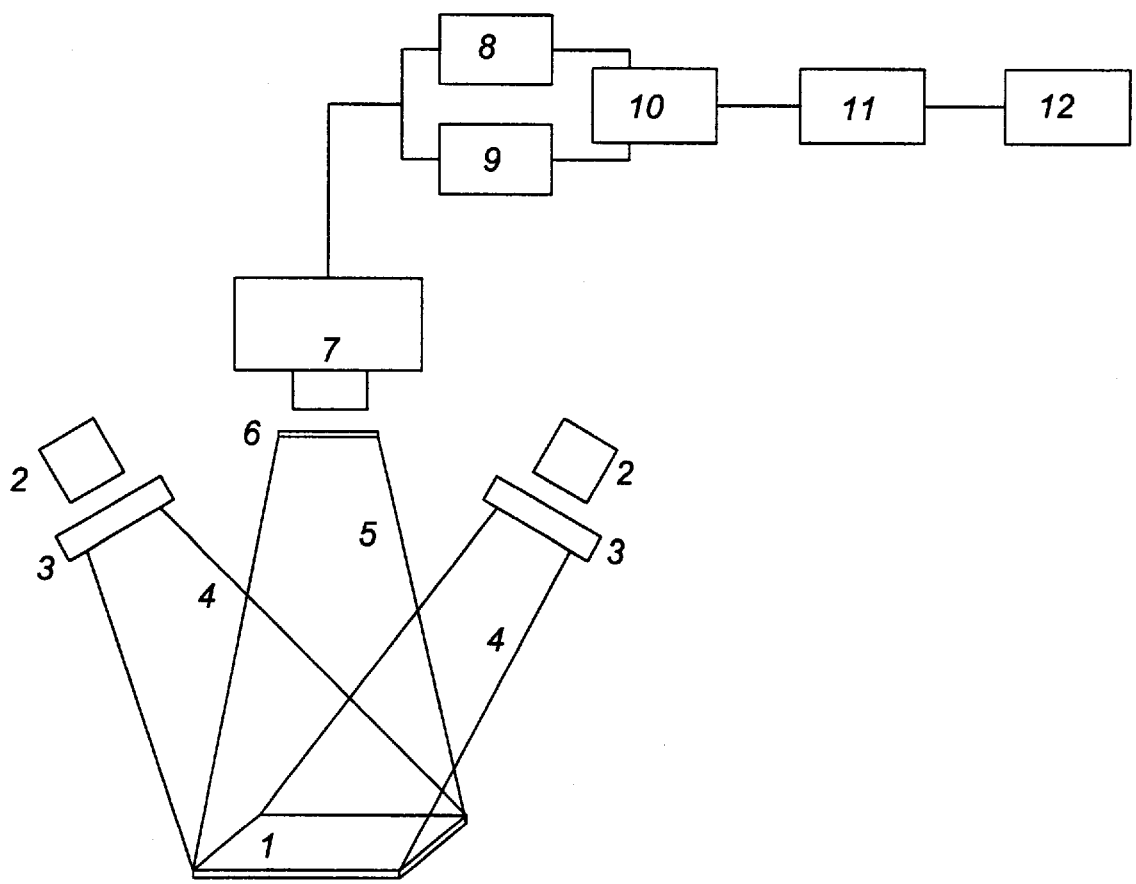
FIG. 1 illustrates the principle of spatial mapping of coating arrays. In this illustration, one or more transparent coatings and substrate (1) is irradiated with a light source (2) via an excitation wavelength selection element (3). The excitation radiation (4) is selected as desired based on the chromophore or luminophore utilized. The emission radiation (5) passes through the emission wavelength selection element (6) and imaging detector (7), where the spectral data is collected in an initial screen (8) before the testing step. The data is further collected at intermediate screen (9) after the testing step. Data from initial (8) and intermediate (9) screens is mathematically processed to generate results of mathematical image processing (10). These results are displayed as structural defects distribution map (11) and unacceptable identified defects in transparent coatings are highlighted in screen (12).
Figure 2:
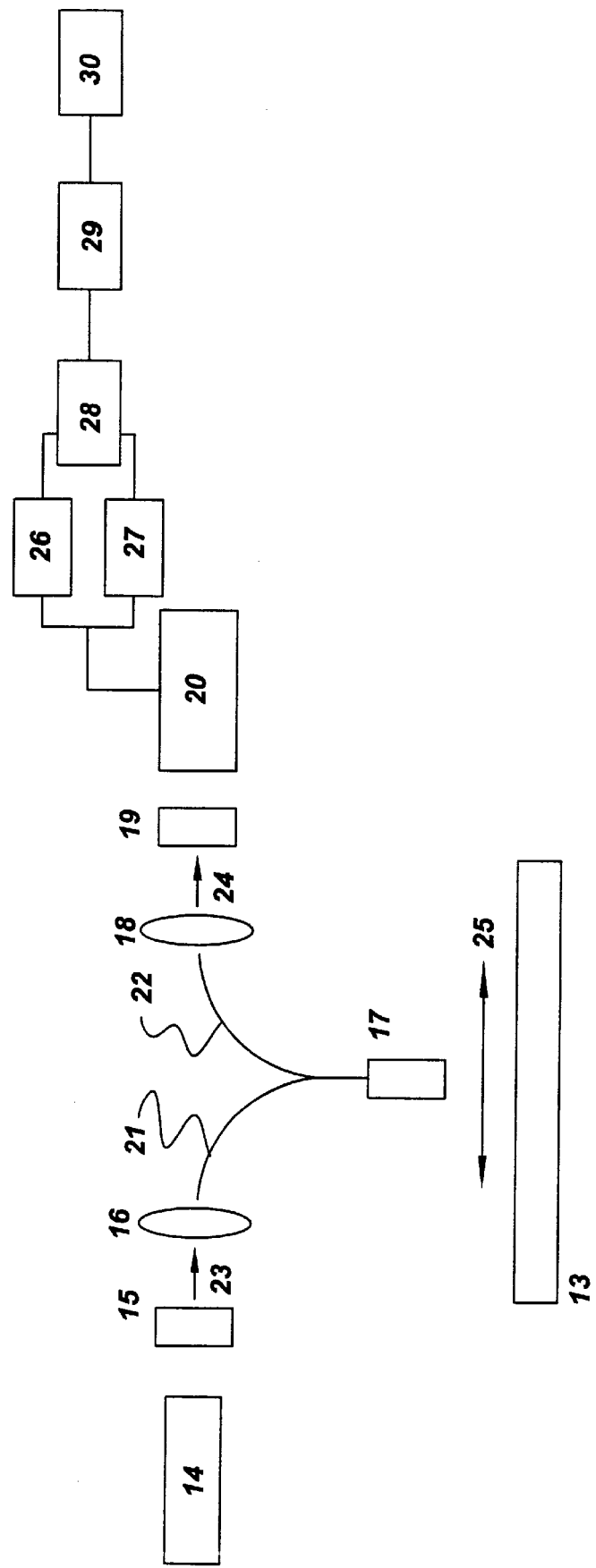
FIG. 2 is depicts a serial analysis method. In this illustration, one or more transparent coatings and substrate (13) is irradiated with a light source (14) via an excitation wavelength selection element (15), focusing lens (16) and an optical fiber (21). The optical fiber (21) delivers light to the probe (17). The excitation radiation (23) is selected as desired based on the chromophore or luminophore utilized. The emission radiation (24) is captured by probe (17), is directed into the optical fiber (22), passes through the lens (18) and emission wavelength selection element (19) and is detected with a detector (20). A plurality of coatings is evaluated by positioning probe (17) over different coatings in the array. Positioning can be achieved by moving the probe (17) and/or coatings on substrate (13). The spectral data from coatings of interest is collected in an initial screen (26) before the testing step. The data is further collected at intermediate screen (27) after the testing step. Data from initial (26) and intermediate (27) screens is mathematically processed to generate results of mathematical processing (28). These results are displayed as structural defects distribution array (29) and unacceptable identified defects in transparent coatings are highlighted in array (30).
Figure 3:
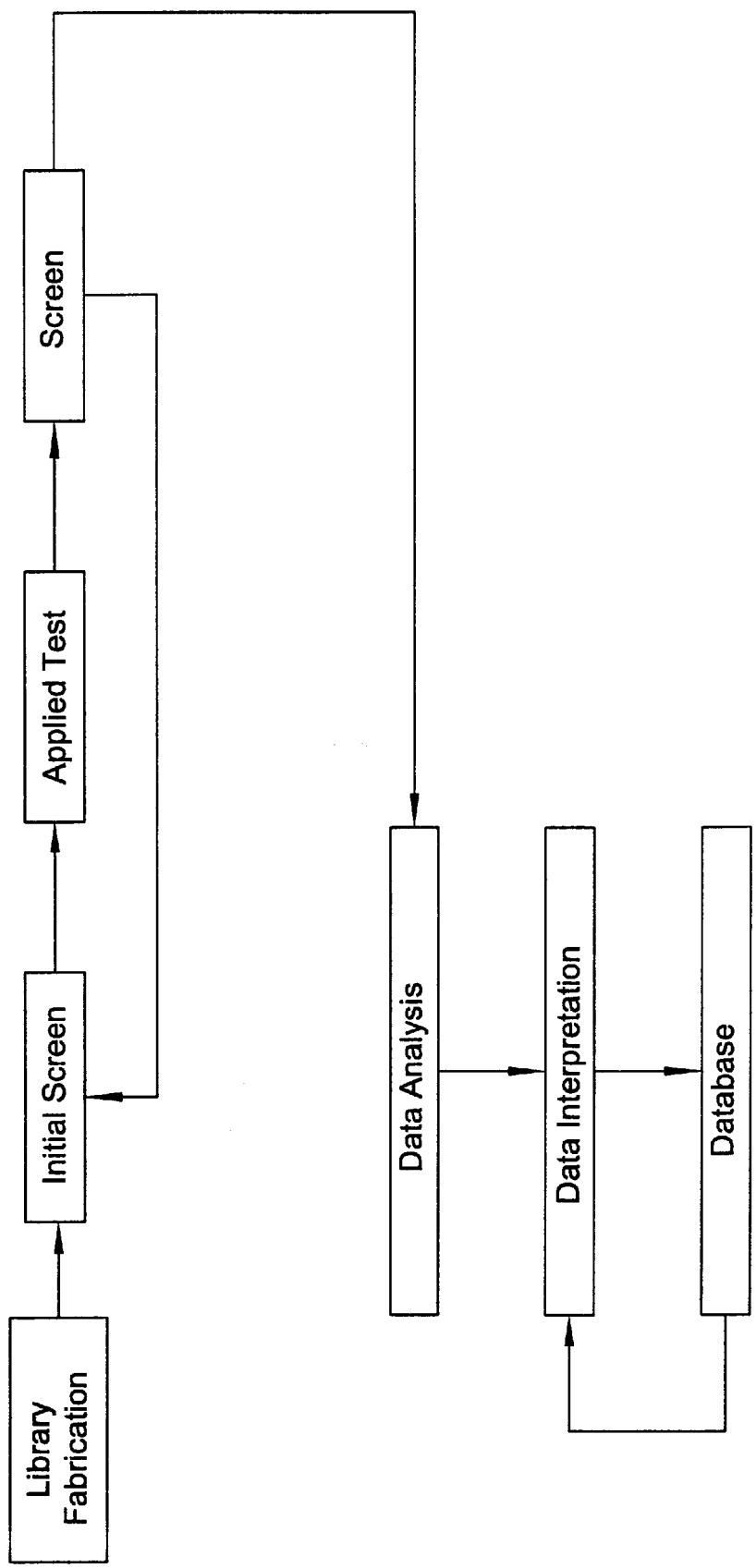
FIG. 3 is a block diagram further illustrating the methodology of the present invention. In this diagram, the coating sample or library to be analyzed is fabricated and run through an initial screen, the test is applied and the screen is conducted a second time. The test can then be reapplied via an iterative process or the data can be analyzed and interpreted over time. This methodology also contemplates an iterative process for the data interpretation and the development of a database of spectral data indicating inherent structural defects characteristics, e.g., adhesion, interdiffusion and abrasion, for a given coating on a given substrate.

Referring to the figures, FIGS. 1 and 2 illustrate a substrate having a thin transparent film thereon. Such a coating is comprised of at least one colorimetric or luminophoric material. The sample is then irradiated with light, preferably via a free space (FIG. 1) or via an optical fiber or waveguide (FIG. 2) and light which is reflected as well as luminescent from the surface of the coating is collected. Such reflection or luminescence spectral data is continuously or periodically collected throughout the structural defect-inducing test(s) until a new baseline for such spectral data is achieved, which in the case of total failure (i.e., removal) of the transparent film from the substrate, without interdiffusion defects will correspond to the background spectrum.

In this regard, the luminescence intensity of the light emitted from such irradiated samples is proportional to the quantum yield of the luminophore and the thickness of the coating according to the following equation:

$$I_o \times \Phi \times \epsilon \times [C_p] \times h \times S,$$

where $I_o$ intensity of excitation light, $\Phi$ is quantum yield of a given luminophore, $\epsilon$ is molar extinction coefficient at the excitation wavelength of a given luminophore, $C_p$ is luminophore concentration in the coating, h, coating thickness, and S is the surface quality coefficient which is proportional to haze value of the coating.

Figure 4:
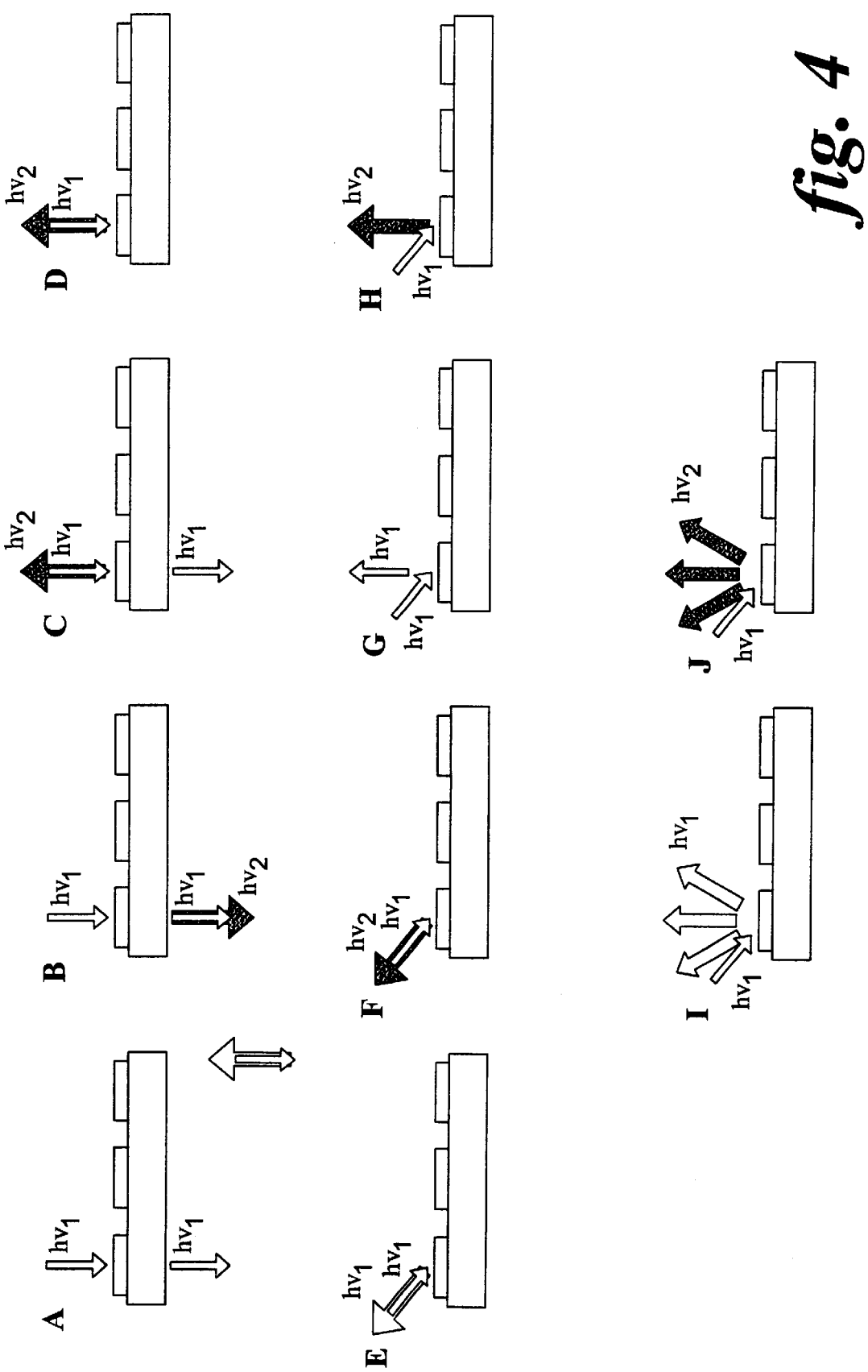
FIG. 4 depicts measurement modes A–J which can be accomplished using the system depicted in FIG. 3. In this figure, A depicts the passage of a given wavelength of irradiation ($hv_1$) passing through the coating and substrate.

In analogous fashion to the analysis of the coating samples in the reflection or luminescence modes, the coating may be analyzed in the transmission and scattering modes and their combinations as illustrated in FIG. 4.

The coatings which may be evaluated by the methodology of the present invention include liquid coatings, i.e., either waterborne or solvent-borne, as well as solventless and powder coatings. Further, such coatings may be cured by a number of different mechanisms depending on the binder/crosslinker system so utilized. For example, some coatings systems are cured at ambient conditions via an autooxidation curing mechanism, such as in alkyds, or by a free radical curing. Additionally, thermal curing is typically required for coatings systems such as melamine containing acrylate coatings or polyurethane coatings.

In free radical initiated UV cure coatings, free radicals are photogenerated and initiate polymerization by adding to vinyl double bonds, primary acrylates. Two classes of photoinitiators are used, those that undergo unimolecular bond cleavage ( e.g. ethers of benzoin, 2,2-dialkyl-2-hydroxyacetophenones, etc.) and those that undergo bimolecular hydrogen abstraction from some other molecule (e.g. phoexcited benzophenone, some tertiary amines, etc.). See, for example, Wicks, Z. W., Jr.; Jones, F. N.; Pappas, S. P. *Organic Coatings: Science and Technology;* Wiley: New York, N.Y., 1999, ch. 28.

In cationic UV cure, cationic photoinitiators are onium salts of strong acids for example, iodonium and sulfonium salts of hexafluoroantimonic and hexafluorophosphoric acids.

Another type of radiation curing is electron beam cure. High energy electron beam can be used to polymerize acrylate coatings.

Moreover, the methodology of the present invention may be utilized in conjunction with such coatings on a variety of substrates, including various metals, composite materials, and plastics.

In one experimental configuration, luminescence measurements were performed on a setup which included a white light source (450-W Xe arc lamp, SLM Instruments, Inc., Urbana, Ill., Model FP-024), a monochromator for selection of the excitation wavelength (SLM Instruments, Inc., Model FP-092), and a portable spectrofluorometer (Ocean Optics, Inc., Dunedin, Fla., Model ST2000). The spectrofluorometer was equipped with a 200-$\mu$m slit, 600-grooves/mm grating blazed at 400 nm and covering the spectral range from 250 to 800 nm with efficiency greater than 30%, and a linear CCD-array detector. Excitation light from the monochromator was focused into one of the arms of a "six-around-one" bifurcated fiber-optic reflection probe (Ocean Optics, Inc., Model R400-7-UV/VIS). Emission light was collected from a sample when the common end of the fiber-optic probe was positioned near the sample at a certain angle to minimize the amount of excitation light reflected from the sample back into the probe. The second arm of the probe was coupled to the spectrofluorometer.

Luminescence imaging measurements were performed using a setup which included a white light source (450-W Xe arc lamp, SLM Instruments, Inc., Urbana, Ill., Model FP-024), a monochromator for selection of the excitation wavelength (SLM Instruments, Inc., Model FP-092), and a CCD camera (Roper Scientific, Trenton, N.J., Model TE/CCD 1100 PF/UV). The excitation wavelength for the luminophore was selected using the monochromator and was directed to the sample. Sample luminescence was collected with the camera. The excitation light was filtered out from being captured by the camera using a long pass optical filter.

EXAMPLE 1

For visualization of adhesion of transparent coatings several luminophores were incorporated into liquid coating formulations. To form a coating, polymethylmethacrylate was dissolved in chloroform at a concentration of about 10% by weight and a solution of a luminophore in chloroform was added to the polymer solution. The concentration of luminophore in polymer solution was about 0.001–5000 ppm. Luminescent dyes selected for doping the coating were inert luminophores, Lumogen F (BASF), types Yellow 083, Orange 240, Red 300, or Violet 570.

Visualization of adhesion of transparent coatings was performed using luminescence imaging by means of the setup described above. Excitation wavelengths for coatings doped with different Lumogen F luminophores are listed in Table 1. Excitation wavelength was selected according to the type of luminophore using the monochromator and was directed to the sample. Luminescence light from the coating was collected with the camera with an integ-ation time of about 1–200 seconds. The excitation light was filtered out from being captured by the camera using a long pass optical filter that transmitted wavelengths 30–100 nm above the wavelength of excitation.

Another setup included a UV excitation source with a strong emission at 365 nm (Ultra-Violet Products, Inc. model B-100A) and a Kodak DC210 digital camera (1152× 864 pixel sensor) for luminescence imaging. The excitation light was filtered out from being captured by the camera using a long pass optical filter that transmitted wavelengths above 400 nm.

TABLE 1

Excitation wavelengths for coatings doped with different Lumogen F luminophores.

| Luminophore type | Range of excitation wavelengths (nm) | Range of emission wavelengths (nm) |
|---|---|---|
| Violet 570 | 200–400 | 400–490 |
| Yellow 083 | 400–480 | 470–560 |
| Orange 240 | 420–530 | 510–570 |
| Red 300 | 420–580 | 570–640 |

One coating formulation was doped with Lumogen Yellow 083 luminophore and was applied onto a quartz plate 5×6 cm using a wet film applicator rod, producing a wet film thickness 20.5 micrometers. A, luminescence image of a coating after a cross cut performed with a cross hatch cutter was obtained. A luminescence image after a tape adhesion test (ASTM Test Method D-3359) was obtained. The coating was subjected to a water resistance test (ASTM Test Method D-870) with an immersion time in hot (70° C.) water for 5 min. Discrimination between the regions with and without coating was obtained with a signal to noise ratio of >50.

Another coating formulation was doped with Lumogen Violet 570 luminophore and was deposited onto a substrate and further tested similarly to the coating described above.

Microscopic analysis of surfaces after water immersion test with the reflected and luminescence light was performed to demonstrate the effectiveness of the luminophore doping of coatings. A confocal laser microscope Zeiss Model LSM 5 Pascal (Carl Zeiss, Jena, Germany) was used to obtain reflected light and luminescence images of the area of the substrate with the coating after the water immersion test.

EXAMPLE 2

Parallel Analysis of Regions of Coating Libraries.

A 12×9-cm sheet of polycarbonate was coated with an array of coating formulations derived from eight mixtures and doped with a red luminophore Lumogen F Red 300, BASF) at a concentration of about 30 ppm in the dry coating. Eight liquid coating formulations were deposited using a liquid handling robot Packard Instrument Co., Model Multiprobe II, Meriden, Conn.). Coating deposition was performed using 8-microliter volumes of coating formulations in methoxypropanol at concentration of 20% solids, pipetting them into separate spatial locations provided with a 48-well mask, and UV curing the film. The 48-element coating library contained eight different coating formulations with six replicates each. Table 2 depicts the formulations used for coating array. Coating formulations in columns 1–5 were from UCB Chemical Corp., North Augusta, S.C. Coating formulations in columns 6–8 were from Sartomer Co., West Chester, Pa.

TABLE 2

Coating formulations

| Column number | Coating formulation name | Description |
|---|---|---|
| 1 | Ebecryl 1290 acrylated urethane | acrylated aliphatic urethane oligomer hexa-functional |
| 2 | Ebecryl 8804 aliphatic urethane | diacrylate - acrylated aliphatic urethane oligomer |

TABLE 2-continued

Coating formulations

| Column number | Coating formulation name | Description |
|---|---|---|
| 3 | Ebecryl 140 acrylate ester | tetraacrylate monomer |
| 4 | DPGDA acrylate ester | dipropylene glycol diacrylate monomer |
| 5 | Ebecryl 8301 acrylated urethane | acrylated aliphatic urethane oligomer |
| 6 | SR 238 | 1,6-hexanediol diacrylate |
| 7 | CD - 401 | cyclohexane dimethanol dimethacrylate - di-functional cycloaliphatic methacrylate monomer. |
| 8 | SR 399 | dipentaerythritol pentaacrylate |

Spatially resolved luminescence mapping of coating array was performed using a setup described above. The excitation wavelength was selected at 350 or 320 nm for excitation of coating or substrate luminescence using the monochromator and was directed to the sample. Luminescence light from the coatings array was collected with the camera with an integration time of about 200 seconds. The excitation light was filtered out from being captured by the camera using a long pass optical filter that transmitted wavelengths above 400 or 345 nm for the excitation of coating or substrate luminescence.

A spatially-resolved map of distribution of luminescence in the array of coatings was obtained. Under the selected excitation and emission conditions, luminescence intensity from the deposited coating elements is higher compared to the luminescence of substrate. Each column in the image may correspond to a certain coating type.

Thus, proper selection of certain excitation and emission conditions permits the luminescence imaging of either coating elements in the array or substrate. This discrimination between coated and uncoated substrate regions using luminescence of coating or substrate permits more detailed and accurate quantification of coating quality parameters such as adhesion than possible by traditional methods.

EXAMPLE 3

Parallel Analysis of Regions of Coatings After Abrasion Test.

A 12×4-cm sheet of polycarbonate was flow coated with a coating derived from a mixture of methyltrimethoxysilane, colloidal silica, and n-butyl alcohol doped with a red luminophore (Lumogen F Red 300, BASF). The coating was dried in air for about 10 min and cured at 130° C. for 30 minutes. Concentration of the luminophore in the cured coating was about 250 ppm. A mask with 11×11 openings was positioned on top of the coating. Circular openings in the mask were 3-mm in diameter with a 5-mm spacing between centers. Seven rows of the coating exposed through the mask were subjected to a stream of 50-$\mu$m $Al_2O_3$ particles at a constant pressure and flow applied with a pencil blaster. The array was automatically advanced under the operating pencil blaster with a speed of 5.5 in/min using an single-axis translation stage. The angle of the pencil blaster was normal to the coating surface. To induce various levels of coating abrasion, the distance to the coating surface was changed from 1 to 4 inches in 0.5-in. increments. Analysis of luminescence was performed on seven abraded rows and regions of coating protected from abrasion by the mask.

Spatially resolved luminescence mapping of coating array was performed using a setup described above. The excitation wavelength was selected at 520 nm using the monochromator and was directed to the sample. Luminescence light from the abraded and unabraded regions of coatings was collected with the camera with an integration time of about 20 seconds. The excitation light was filtered out from being captured by the camera using a long pass optical filter that transmitted wavelengths above 610 nm.

EXAMPLE 4

A 12×4-cm sheet of polycarbonate was flow coated with a coating derived from a mixture of methyltrimethoxysilane, colloidal silica, and n-butyl alcohol doped with a red luminophore (Lumogen F Red300, BASF). The coating was dried in air for about 10 min and cured at 130° C. for 30 minutes. Concentration of the luminophore in the cured coating was about 250 ppm. A mask with 11×11 openings was positioned on top of the coating. Circular openings in the mask were 3-mm in diameter with a 5-mm spacing between centers. Seven rows of the coating exposed through the mask were subjected to a stream of 50-$\mu$m $Al_2O_3$ particles at a constant pressure and flow applied with a pencil blaster. The array was automatically advanced under the operating pencil blaster with a speed of 5.5 in/min using an single-axis translation stage. The angle of the pencil blaster was normal to the coating surface. To induce various levels of coating abrasion, the distance to the coating surface was changed from 1 to 4 inches in 0.5-in. increments. Analysis of luminescence was performed on seven abraded rows and regions of coating protected from abrasion by the mask.

Spectral determinations of luminescence were performed on a setup as described above in the "Spectroscopic Setup" section of this Experimental Section.

FIG. 5 demonstrates the variation of intensity of luminescence from the coating as a function of coating/sand blaster distance. The error bars are one standard deviation from the mean of 11 measurements (a whole row of coatings). Two measurements (runs 1 and 2) over the same coating regions performed at different times and with about 0.5–1 mm offsets from each other show no differences indicating even abrasion of material at distances 2–4 in. between the pencil blaster and coating. The sand blasting increases coating abrasion upon decreasing the distance between the pencil blaster and coating. The initial increase of luminescence at low abrasion levels is caused by the increased effective illumination area on the coating due to the more scattering of excitation light from the coating and subsequent increase of luminescence intensity. Upon further removal of the coating at short blaster/coating distances, luminescence decreases because of the removal of coating down to the substrate.

We claim:

1. A method for quantifying inherent structural defects of a coating composition on a given substrate, which comprises:
    (a) providing at least one coating sample having incorporated therein at least one colorimetric or luminescent material;
    (b) irradiating said coating sample with light of a preselected wavelength, before, during and/or after subjecting said sample to at least one structural defect-inducing test;
    (c) collecting spectral data emitted from said sample; and
    (d) applying a pre-determined test to said spectral data to determine whether said sample meets pre-selected criteria.

2. The method of claim 1, wherein the coating sample is comprised of at least one luminescent material and is irradiated with ultraviolet, visible, and/or near infrared light.

3. The method of claim 1, wherein the coating sample is comprised of at least one colorimetric material.

4. The method of claim 1, wherein the coating sample is comprised of at least one luminescent material.

5. The method of claim 1, wherein the colorimetric or luminescent material is selected from dyes, pigments, metal and semiconductor nanoparticles, nanotubes and nanowires.

6. The method of claim 1, wherein the luminescent or colorimetric material is selected from the group consisting of polyazaindacene dyes; coumarin dyes; hydrocarbon and substituted hydrocarbon dyes; polycyclic aromatic hydrocarbons; scintillation dyes; aryl- and heteroaryl-substituted polyolefins ($C_2$–$C_8$ olefin portion); carbocyanine dyes; phthalocyanine dyes and pigments; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; and xanthene dyes.

7. The method of claim 1, wherein the luminescent or colorimetric material is selected from the group consisting of
    5-Amino-9-diethyliminobenzo(a)phenoxazonium Perchlorate;
    7-Amino-4-methylcarbostyryl;
    7-Amino-4-methylcoumarin;
    7-Amino-4-trifluoromethylcoumarin;
    3-(2'-Benzimidazolyl)-7-N,N-diethylaminocoumarin;
    3-(2'-Benzothiazolyl)-7-diethylaminocoumarin;
    2-(4-Biphenylyl)-5-(4-t-butylphenyl)-1,3,4-oxadiazole;
    2-(4-Biphenylyl)-5-phenyl-1,3,4-oxadiazole;
    2-(4-Biphenyl)-6-phenylbenzoxazole-1,3;
    2,5-Bis-(4-biphenylyl)-1,3,4-oxadiazole;
    2,5-Bis-(4-biphenylyl)-oxazole;
    4,4-Bis-(2-butyloctyloxy)-p-quaterphenyl;
    p-Bis(o-methylstyryl)-benzene;
    5,9-Diaminobenzo(a)phenoxazonium Perchlorate;
    4-Dicyanomethylene-2-methyl-6-(p-dimethylaminostyryl)-4H-pyran;
    1,1'-Diethyl-2,2'-carbocyanine Iodide;
    1,1'-Diethyl-4,4'-carbocyanine Iodide;
    3,3'-Diethyl-4,4',5,5'-dibenzothiatricarbocyanine Iodide;
    1,1'-Diethyl-4,4'-dicarbocyanine Iodide;
    1,1'-Diethyl-2,2'-dicarbocyanine Iodide;
    3,3'-Diethyl-9,11-neopentylenethiatricarbocyanine Iodide;
    1,3'-Diethyl-4,2'-quinolyloxacarbocyanine Iodide;
    1,3'-Diethyl-4,2'-quinolylthiacarbocyanine Iodide;
    3-Diethylamino-7-diethyliminophenoxazonium Perchlorate;
    7-Diethylamino-4-methylcoumarin;
    7-Diethylamino-4-trifluoromethylcoumarin;
    7-Diethylaminocoumarin;
    3,3'-Diethyloxadicarbocyanine Iodide;
    3,3'-Diethylthiacarbocyanine Iodide;
    3,3'-Diethylthiadicarbocyanine Iodide;
    3,3'-Diethylthiatricarbocyanine Iodide;
    4,6-Dimethyl-7-ethylaminocoumarin;
    2,2'-Dimethyl-p-quaterphenyl;

2,2-Dimethyl-p-terphenyl;
7-Dimethylamino-1-methyl-4-methoxy-8-azaquinolone-2;
7-Dimethylamino-4-methylquinolone-2;
7-Dimethylamino-4-trifluoromethylcoumarin;
2-(4-(4-Dimethylaminophenyl)-1,3-butadienyl)-3-ethylbenzothiazolium Perchlorate;
2-(6-(p-Dimethylaminophenyl)-2,4-neopentylene-1,3,5-hexatrienyl)-3-methylbenzothiazolium Perchlorate;
2-(4-(p-Dimethylaminophenyl)-1,3-butadienyl)-1,3,3-trimethyl-3H-indolium Perchlorate;
3,3'-Dimethyloxatricarbocyanine Iodide;
2,5-Diphenylfuran;
2,5-Diphenyloxazole;
4,4'-Diphenylstilbene;
1-Ethyl-4-(4-(p-Dimethylaminophenyl)-1,3-butadienyl)-pyridinium Perchlorate;
1-Ethyl-2-(4-(p-Dimethylaminophenyl)-1,3-butadienyl)-pyridinium Perchlorate;
1-Ethyl-4-(4-(p-Dimethylaminophenyl)-1,3-butadienyl)-quinolium Perchlorate;
3-Ethylamino-7-ethylimino-2,8-dimethylphenoxazin-5-ium Perchlorate;
9-Ethylamino-5-ethylamino-10-methyl-5H-benzo(a)phenoxazonium Perchlorate;
7-Ethylamino-6-methyl-4-trifluoromethylcoumarin;
7-Ethylamino-4-trifluoromethylcoumarin;
1,1',3,3,3',3'-Hexamethyl-4,4', 5,5'-dibenzo-2,2'-indotricarboccyanine Iodide;
1,1',3,3,3',3'-Hexamethylindodicarbocyanine Iodide;
1,1',3,3,3',3'-Hexamethylindotricarbocyanine Iodide;
2-Methyl-5-t-butyl-p-quaterphenyl;
N-Methyl-4-trifluoromethylpiperidino-<3,2-g>coumarin;
3-(2'-N-Methylbenzimidazolyl)-7-N,N-diethyaminocoumarin;
2-(1-Naphthyl)-5-phenyloxazole;
2,2'-p-Phenylen-bis(5-phenyloxazole);
3,5,3"",5""-Tetra-t-butyl-p-sexiphenyl;
3,5,3"",5""-Tetra-t-butyl-p-quinquephenyl;
2,3,5,6-1H,4H-Tetrahydro-9-acetylquinolizino-<9,9a,1-gh>coumarin;
2,3,5,6-1H,4H-Tetrahydro-9-carboethoxyquinolizino-<9,9a,1-gh>coumarin;
2,3,5,6-1H,4H-Tetrahydro-8-methylquinolizino-<9,9a,1-gh>coumarin;
2,3,5,6-1H,4H-Tetrahydro-9-(3-pyridyl)-quinolizino-<9,9a,1-gh>coumarin;
2,3,5,6-1H,4H-Tetrahydro-8-trifluoromethylquinolizino-<9,9a,1-gh>coumarin;
2,3,5,6-1H,4H-Tetrahydroquinolizino-<9,9a,1-gh>coumarin;
3,3',2",3'"-Tetramethyl-p-quaterphenyl;
2,5,2"",5""-Tetramethyl-p-quinquephenyl;
P-terphenyl;
P-quaterphenyl;
Nile Red;
Rhodamine 700;
Oxazine 750;
Rhodamine 800;
IR 125;
IR 144;
IR 140;
IR 132;
IR 26;
IR 5;
Diphenylhexatriene;
Diphenylbutadiene;
Tetraphenylbutadiene;
Naphthalene;
Anthracene;
Pyrene;
Chrysene;
Rubrene;
Coronene;
Phenanthrene;
Fluorene;
Aluminum phthalocyanine; and
Platinum octaethylporphyrin.

8. The method of claim 1, wherein said structural defect-inducing test is selected from the group consisting of a pull test, a peel test, a micro-scratch test, a supersonic water jet test, a stress-wave emission test, a crosscut test, and a contrast analysis test.

9. The method of claim 1, wherein the structural defect-inducing test is a test which utilizes at least one defect-inducing method selected from, sonication, water immersion, falling abrasive test, abrasive blast test, rotating discs test, and rectilinear motion test.

10. The method of claim 1, wherein the structural defect-inducing test is ASTM D 3359.

11. The method of claim 1, wherein the structural defect-inducing test is ASTM D 870.

12. The method of claim 1, wherein the coating composition is applied to the substrate in liquid form.

13. The method of claim 12, wherein said liquid has a viscosity of from 0.1 to 100,000 centipoise (cP).

14. The method of claim 1, wherein coating composition has a pencil hardness of from 6B to HB, when tested according to ASTM D 3363.

15. The method of claim 1, wherein the coating composition has a pencil hardness of from F to 6 H, when tested according to ASTM D 3363.

16. The method of claim 1, wherein the coating composition is on a flexible substrate.

17. The method of claim 1, wherein the coating composition is on a rigid substrate.

18. The method of claim 1, wherein the coating composition has been delaminated from the substrate.

19. The method of claim 1, wherein the coating sample has been cured by a method selected from the group consisting of radiation (UV and electron beam) curing, oxidative curing, thermal curing, and moisture curing.

20. A method for quantifying interdiffusion of a coating into a given substrate, which comprises:
   (a) providing at least one coating sample having incorporated therein at least one colorimetric or luminescent material;
   (b) irradiating said coating sample with light of a preselected wavelength, before, during and/or after subjecting said sample to at least one structural defect-inducing test;
   (c) collecting spectral data emitted from said sample; and (d) comparing a steady state spectral data baseline achieved after removal of said coating to spectral data acquired by irradiation of an uncoated substrate.

21. A method for quantifying inherent structural defects of coatings in an array of samples coated with coating compositions on at least one given substrate, which comprises:
- (a) providing an array of coating samples having incorporated therein at least one colorimetric or luminescent dye;
- (b) irradiating said array of coating samples with light of a pre-selected wavelength, before, during and/or after subjecting said array of coating samples to at least one structural defect-inducing test;
- (c) collecting spectral data emitted from said array of coating samples; and
- (d) applying a pre-determined test to said spectral data to determine which of said samples meet pre-selected criteria.

22. The method of claim 21, wherein the coating sample is comprised of at least one luminescent material and is irradiated with ultraviolet, visible, and/or near infrared light.

23. The method of claim 21, wherein the coating sample is comprised of at least one colorimetric material.

24. The method of claim 21, wherein the coating sample is comprised of at least one luminescent material.

25. The method of claim 21, wherein the colorimetric or luminescent material is selected from dyes, pigments, metal and semiconductor nanoparticles, nanotubes and nanowires.

26. The method of claim 21, wherein the luminescent or colorimetric material is selected from the group consisting of polyazaindacene dyes; coumarin dyes; hydrocarbon and substituted hydrocarbon dyes; polycyclic aromatic hydrocarbons; scintillation dyes; aryl- and heteroaryl-substituted polyolefins ($C_2$–$C_8$ olefin portion); carbocyanine dyes; phthalocyanine dyes and pigments; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; and xanthene dyes.

27. The method of claim 21, wherein the luminescent or colorimetric material is selected from the group consisting of 5-Amino-9-diethyliminobenzo(a)phenoxazonium Perchlorate;
7-Amino-4-methylcarbostyryl;
7-Amino-4-methylcoumarin;
7-Amino-4-trifluoromethylcoumarin;
3-(2'-Benzimidazolyl)-7-N,N-diethylaminocoumarin;
3-(2'-Benzothiazolyl)-7-diethylaminocoumarin;
2-(4-Biphenylyl)-5-(4-t-butylphenyl)-1,3,4-oxadiazole;
2-(4-Biphenylyl)-5-phenyl-1,3,4-oxadiazole;
2-(4-Biphenyl)-6-phenylbenzoxazole-1,3;
2,5-Bis-(4-biphenylyl)-1,3,4-oxadiazole;
2,5-Bis-(4-biphenylyl)-oxazole;
4,4-Bis-(2-butyloctyloxy)-p-quaterphenyl;
p-Bis(o-methylstyryl)-benzene;
5,9-Diaminobenzo(a)phenoxazonium Perchlorate;
4-Dicyanomethylene-2-methyl-6-(p-dimethylaminostyryl)-4H-pyran;
1,1'-Diethyl-2,2'-carbocyanine Iodide;
1,1'-Diethyl-4,4'-carbocyanine Iodide;
3,3'-Diethyl-4,4',5,5'-dibenzothiatricarbocyanine Iodide;
1,1'-Diethyl-4,4'-dicarbocyanine Iodide;
1,1'-Diethyl-2,2'-dicarbocyanine Iodide;
3,3'-Diethyl-9,11-neopentylenethiatricarbocyanine Iodide;
1,3'-Diethyl-4,2'-quinolyloxacarbocyanine Iodide;
1,3'-Diethyl-4,2'-quinolylthiacarbocyanine Iodide;
3-Diethylamino-7-diethyliminophenoxazonium Perchlorate;
7-Diethylamino-4-methylcoumarin;
7-Diethylamino-4-trifluoromethylcoumarin;
7-Diethylaminocoumarin;
3,3'-Diethyloxadicarbocyanine Iodide;
3,3'-Diethylthiacarbocyanine Iodide;
3,3'-Diethylthiadicarbocyanine Iodide;
3,3'-Diethylthiatricarbocyanine Iodide;
4,6-Dimethyl-7-ethylaminocoumarin;
2,2'-Dimethyl-p-quaterphenyl;
2,2-Dimethyl-p-terphenyl;
7-Dimethylamino-1-methyl-4-methoxy-8-azaquinolone-2;
7-Dimethylamino-4-methylquinolone-2;
7-Dimethylamino-4-trifluoromethylcoumarin;
2-(4-(4-Dimethylaminophenyl)-1,3-butadienyl)-3-ethylbenzo-thiazolium Perchlorate;
2-(6-(p-Dimethylaminophenyl)-2,4-neopentylene- 1,3,5-hexatrienyl)-3-methylbenzothiazolium Perchlorate;
2-(4-(p-Dimethylaminophenyl)-1,3-butadienyl)- 1,3,3-trimethyl-3H-indolium Perchlorate;
3,3'-Dimethyloxatricarbocyanine Iodide;
2,5-Diphenylfuran;
2,5-Diphenyloxazole;
4,4'-Diphenylstilbene;
1-Ethyl-4-(4-(p-Dimethylaminophenyl)-1,3-butadienyl)-pyridinium Perchlorate;
1-Ethyl-2-(4-(p-Dimethylaminophenyl)-1,3-butadienyl)-pyridinium Perchlorate;
1-Ethyl-4-(4-(p-Dimethylaminophenyl)-1,3-butadienyl)-quinolium Perchlorate;
3-Ethylamino-7-ethylimino-2,8-dimethylphenoxazin-5-ium Perchlorate;
9-Ethylamino-5-ethylamino-10-methyl-5H-benzo(a)phenoxazonium Perchlorate;
7-Ethylamino-6-methyl-4-trifluorometbylcoumarin;
7-Ethylamino-4-trifluoromethylcoumarin;
1,1',3,3,3',3'-Hexamethyl-4,4', 5,5'-dibenzo-2,2'-indotricarboccyanine Iodide;
1,1',3,3,3',3'-Hexamethylindodicarbocyanine Iodide;
1,1',3,3,3',3'-Hexamethylindotricarbocyanine Iodide;
2-Methyl-5-t-butyl-p-quaterphenyl;
N-Methyl-4-trifluoromethylpiperidino-<3,2-g>coumarin;
3-(2'-N-Methylbenzimidazolyl)-7-N,N-ciethyaminocoumarin;
2-(1-Naphthyl)-5-phenyloxazole;
2,2'-p-Phenylen-bis(5-phenyloxazole);
3,5,3'''',5'''-Tetra-t-butyl-p-sexiphenyl;
3,5,3'''',5'''-Tetra-t-butyl-p-quinquephenyl;
2,3,5,6-1H,4H-Tetrahydro-9-acetylquinolizino-<9,9a,1-gh>coumarin;
2,3,5,6-1H,4H-Tetrahydro-9-carboethoxyquinolizino-<9,9a,1-gh>coumarin;

2,3,5,6-1H,4H-Tetrahydro-8-methylquinolizino-<9,9a,1-gh>coumarin;

2,3,5,6-1H,4H-Tetrahydro-9-(3-pyridyl)-quinolizino-<9,9a,1-gh>coumarin;

2,3,5,6-1H,4H-Tetrahydro-8-trifluoromethylquinolizino-<9,9a,1-gh>coumarin;

2,3,5,6-1H,4H-Tetrahydroquinolizino-<9,9a,1-gh>coumarin;

3,3',2'',3'''-Tetramethyl-p-quaterphenyl;

2,5,2'''',5''''-Tetramethyl-p-quinquephenyl;

P-terphenyl;

P-quaterphenyl;

Nile Red;

Rhodamine 700;

Oxazine 750;

Rhodamine 800;

IR 125;

IR 144;

IR 140;

IR 132;

IR 26;

IR 5;

Diphenylhexatriene;

Diphenylbutadiene;

Tetraphenylbutadiene;

Naphthalene;

Anthracene;

Pyrene;

Chrysene;

Rubrene;

Coronene;

Phenanthrene;

Fluorene;

Aluminum phthalocyanine; and

Platinum octaethylporphyrin.

28. The method of claim 21, wherein said structural defect-inducing test is selected from the group consisting of a pull test, a peel test, a micro-scratch test, a supersonic water jet test, a stress-wave emission test, a crosscut test, and a contrast analysis test.

29. The method of claim 21, wherein the structural defect-inducing test is a test which utilizes at least one defect-inducing method selected from, sonication, water immersion, falling abrasive test, abrasive blast test, rotating discs test, and rectilinear motion test.

30. The method of claim 21, wherein the structural defect-inducing test is ASTM D 3359.

31. The method of claim 21, wherein the structural defect-inducing test is ASTM D 870.

32. The method of claim 21, wherein the coating composition is applied to the substrate in liquid form.

33. The method of claim 32, wherein said liquid has a viscosity of from 0.1 to 100,000 centipoise (cP).

34. The method of claim 21, wherein coating composition has a pencil hardness of from 6B to HB, when tested according to ASTM D 3363.

35. The method of claim 21, wherein the coating composition has a pencil hardness of from F to 6 H, when tested according to ASTM D 3363.

36. The method of claim 21, wherein the coating composition is on a flexible substrate.

37. The method of claim 21, wherein the coating composition is on a rigid substrate.

38. The method of claim 21, wherein the coating composition has been delaminated from the substrate.

39. The method of claim 21, wherein the coating sample has been cured by a method selected from the group consisting of radiation (UV and electron beam) curing, oxidative curing, thermal curing, and moisture curing.

40. A method for quantifying inherent structural defects of a coating composition comprised of a given material on a given substrate, which comprises:

(a) providing at least one coating sample comprising a substrate having coated thereon at least one coating material, said coating material having incorporated therein at least one colorimetric or luminescent material;

(b) subjecting said sample to at least one structural defect-inducing test, while collecting coating material which is removed from said sample by said test;

(c) irradiating said removed coating material with light of a pre-selected wavelength;

(d) collecting spectral data emitted from said removed coating material; and (e) applying a pre-determined test to said spectral data to determine whether said sample meets pre-selected criteria.

41. The method of claim 40, wherein the removed coating material is comprised of at least one luminescent material and is irradiated with ultraviolet, visible, and/or near infrared light.

42. The method of claim 40, wherein the removed coating material is comprised of at least one colorimetric material.

43. The method of claim 40, wherein the colorimetric or luminescent material is selected from dyes, pigments, metal and semiconductor nanoparticles, nanotubes and nanowires.

44. The method of claim 40, wherein the luminescent or colorimetric material is selected from the group consisting of polyazaindacene dyes; coumarin dyes; hydrocarbon and substituted hydrocarbon dyes; polycyclic aromatic hyrdocarbons; scintillation dyes; aryl- and heteroaryl-substituted polyolefins ($C_2$–$C_8$ olefin portion); carbocyanine dyes; phthalocyanine dyes and pigments; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; and xanthene dyes.

45. The method of claim 40, wherein said structural defect-inducing test is selected from the group consisting of a pull test, a peel test, a micro-scratch test, a supersonic water jet test, a stress-wave emission test, a crosscut test, and a contrast analysis test.

46. The method of claim 40, wherein the structural defect-inducing test is a test which utilizes at least one defect-inducing method selected from, sonication, water immersion, falling abrasive test, abrasive blast test, rotating discs test, and rectilinear motion test.

47. The method of claim 40, wherein the structural defect-inducing test is ASTM D 3359.

48. The method of claim 40, wherein the structural defect-inducing test is ASTM D 870.

49. The method of claim 40, wherein the coating sample has been cured by a method selected from the group consisting of radiation (UV and electron beam) curing, oxidative curing, thermal curing, and moisture curing.

50. A method for quantifying interdiffusion of a substrate into a coating on a given substrate, which comprises:

(a) providing at least one coating sample comprising a substrate having coated thereon at least one coating material, said coating material having incorporated therein at least one colorimetric or luminescent material;

(b) subjecting said sample to at least one structural defect-inducing test, while collecting removed coating material which is removed from said sample by said test;

(c) irradiating said removed coating material with light of a pre-selected wavelength;

(d) collecting spectral data emitted from said removed coating material;

(e) comparing a steady state spectral data baseline achieved after removal of said coating to spectral data acquired by irradiation of an coated substrate which has not been subjected to said at least one structural defect-inducing test.

* * * * *